US010583183B2

(12) United States Patent
Magliocco et al.

(10) Patent No.: US 10,583,183 B2
(45) Date of Patent: Mar. 10, 2020

(54) IMMUNE GENE SIGNATURES IN UROTHELIAL CARCINOMA (UC)

(71) Applicant: H. Lee Moffitt Cancer Center and Research Institute, Inc., Tampa, FL (US)

(72) Inventors: Anthony M. Magliocco, Tampa, FL (US); James J. Mulé, Odessa, FL (US); Anders Erik Berglund, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 254 days.

(21) Appl. No.: 15/128,560

(22) PCT Filed: Apr. 10, 2015

(86) PCT No.: PCT/US2015/025288
§ 371 (c)(1),
(2) Date: Sep. 23, 2016

(87) PCT Pub. No.: WO2015/157623
PCT Pub. Date: Oct. 15, 2015

(65) Prior Publication Data
US 2017/0175199 A1 Jun. 22, 2017

Related U.S. Application Data

(60) Provisional application No. 61/978,584, filed on Apr. 11, 2014.

(51) Int. Cl.
*A61K 39/00* (2006.01)
*C12Q 1/6886* (2018.01)
*C12Q 1/6883* (2018.01)

(52) U.S. Cl.
CPC ........ *A61K 39/0011* (2013.01); *C12Q 1/6886* (2013.01); *C12Q 1/6883* (2013.01); *C12Q 2600/112* (2013.01); *C12Q 2600/158* (2013.01)

(58) Field of Classification Search
None
See application file for complete search history.

(56) References Cited

U.S. PATENT DOCUMENTS

| | | |
|---|---|---|
| 7,741,345 B2 | 6/2010 | Cannizzaro et al. |
| 2009/0215053 A1 | 8/2009 | Galon et al. |
| 2011/0059459 A1 | 3/2011 | Taron Roca et al. |
| 2013/0034540 A1 | 2/2013 | Mule et al. |

FOREIGN PATENT DOCUMENTS

| | | |
|---|---|---|
| WO | WO 2009/114547 | 9/2009 |
| WO | WO 2011/094483 | 8/2011 |
| WO | WO 2013/173223 | 11/2013 |

OTHER PUBLICATIONS

American Cancer Society ("Whatis Cancer Immunotherapy" downloaded Apr. 29, 2018 from https://www.cancer.org/treatment/treatments-and-side-effects/treatmentAmerican Cancer Society (What-types/immunotherapy/what-is-immunotherapy.html) (Year: 2018).*
Brooks (Genome Res. Feb. 2012;22(2):183-7) (Year: 2012).*
Venet et al (PLoS Comput Biol. Oct. 2011;7(10):e1002240) (Year: 2011).*
American Cancer Society ("Immunotherapy for Bladder Cancer" downloaded Apr. 29, 2018 from https://www.cancer.org/cancer/bladder-cancer/treating/immunotherapy-for-bladder-cancer.html) (Year: 2018).*
Travis et al (J Natl Cancer Inst. Apr. 5, 1995;87(7):524-30) (Year: 1995).*
Aggen et al (Journal for ImmunoTherapy of Cancer (2017) 5:94) (Year: 2017).*
Auerbach et al (Cancer and Metastasis Reviews, 2000, 19: 167-172) (Year: 2000).*
Gura T (Science, 1997, 278(5340): 1041-1042, encloses 1-5) (Year: 1997).*
Jain RK (Scientific American, Jul. 1994,58-65) (Year: 1994).*
Cheng et al (Oncogenesis (2018) 7:2) (Year: 2018).*
NCI Dictionary of Cancer Terms, downloaded from https://www.cancer.gov/publications/dictionaries/cancer-terms/def/immune-checkpoint-inhibitor on Dec. 2, 2018 (Year: 2018).*
AJCC: Urinary bladder. In: Edge SB, Byrd DR, Compton CC, et al., eds.: AJCC Cancer Staging Manual. 7th ed. New York, NY: Springer, 2010, pp. 497-505.
Alexandrescu et al., "Immunotherapy for melanoma: current status and perspectives," J Immunother, Jul.-Aug. 2010, 33(6):570-90.
Aspord et al., "Breast cancer instructs dendritic cells to prime interleukin 13-secreting CD4+ T cells that facilitate tumor development," J Exp Med, 2007, 204: 1037-1047.
Bell et al., "In breast carcinoma tissue, immature dendritic cells reside within the tumor, whereas mature dendritic cells are located in peritumoral areas," J Exp Med, Nov. 1999, 190: 1417-1426.
Coppola and Mule, "Ectopic lymph nodes within human solid tumors," J Clin Oncol, Sep. 2008, 26: 4369-4370.
Coronella et al., "Antigen-driven oligoclonal expansion of tumor-infiltrating B cells in infiltrating ductal carcinoma of the breast," J Immunol, 2002, 169: 1829-1836.
Coronella-Wood and Hersh, "Naturally occurring B-cell responses to breast cancer," Cancer Immunol Immunother, Dec. 2003, 52:715-738.
Curiel et al., "Specific recruitment of regulatory T cells in ovarian carcinoma fosters immune privilege and predicts reduced survival," Nat Med, Sep. 2004, 10: 942-949.
Dieu-Nosjean et al., "Long-term survival for patients with non-small-cell lung cancer with intratumoral lymphoid structures," J Clin Oncol, Sep. 2008, 26: 4410-4417.

(Continued)

*Primary Examiner* — Brian Gangle
*Assistant Examiner* — Andrea K McCollum
(74) *Attorney, Agent, or Firm* — Fish & Richardson P.C.

(57) ABSTRACT

This invention relates to methods for treating subjects with bladder cancer, such as urothelial carcinoma, based on mRNA expression levels of chemokines.

4 Claims, 11 Drawing Sheets

(56) References Cited

OTHER PUBLICATIONS

Eggermont et al., "Anti-CTLA-4 antibody adjuvant therapy in melanoma," Semin Oncol., Oct. 2010, 37(5):455-9.
Eisenthal et al., "Expression of dendritic cells in ovarian tumors correlates with clinical outcome in patients with ovarian cancer," Hum Pathol, Aug. 2001, 32: 803-807.
Ganesan and Bakhshi, "Systemic therapy for melanoma," Natl Med J India, Jan.-Feb. 2010, 23(1):21-7.
Golovina and Vonderheide, "Regulatory T cells: overcoming suppression of T-cell immunity," Cancer J. Jul.-Aug. 2010, 16(4):342-7.
International Preliminary Report on Patentability in International Application No. PCT/US2015/025288, dated Oct. 12, 2016, 7 pages.
International Search Report and Written Opinion in International Application No. PCT/US15/25288, dated Jul. 28, 2015, 13 pages.
Klinke, "A multiscale systems perspective on cancer, immunotherapy, and Interleukin-12," Mol Cancer, Sep. 2010, 9:242.
Kruger et al., "Immune based therapies in cancer," Histol Histopathol. Jun. 2007;22(6):687-96.
Kurabayashi et al., "Distribution of tumor-infiltrating dendritic cells in human non-small cell lung carcinoma in relation to apoptosis," Pathol Int, 2004, 54: 302-310.
Michael-Robinson et al., "Tumour infiltrating lymphocytes and apoptosis are independent features in colorectal cancer stratified according to microsatellite instability status," Gut, 2001, 48: 360-366.
Moschella et al., "Combination strategies for enhancing the efficacy of immunotherapy in cancer patients," Ann NY Acad Sci., Apr. 2010, 1194: 169-78.
Nagorsen et al., "Tumor-infiltrating macrophages and dendritic cells in human colorectal cancer: Relation to local regulatory T cells, systemic T-cell response against tumor-associated antigens and survival," J Transl Med, 2007, 5: 62.
Powles et al., "MPDL3280A (anti-PD-LI) treatment leads to clinical activity in metastatic bladder cancer," Nature, Nov. 2014, 515(7528):558-62.
Ropponen et al., Prognostic value of tumour-infiltrating lymphocytes (TILs) in colorectal cancer, J Pathol, Jul. 1997, 182: 318-324.
Shiao et al., "Immune microenvironments in solid tumors: new targets for therapy," Genes & Dev., 2011, 25: 2559-2572.
Singh et al., "Lymphoid neogenesis and immune infiltration in aged liver," Hepatology, 2008, 47:1680-1690.
Tarhini and Iqbal, "CTLA-4 blockade: therapeutic potential in cancer treatments," Onco Targets Ther, Feb. 2010, 3:15-25.
Topalian, et al., Safety, Activity, and Immune Correlates of Anti-PD-1 Antibody in Cancer, NEJM, Jun. 2012, 366(26): 2443-2454.
Welsh et al., "Iterative rank-order normalization of gene expression microarray data," BMC Bioinformatics, 2013, 14(1):153.
Zeid and Muller, "S100 positive dendritic cells in human lung tumors associated with cell differentiation and enhanced survival," Pathology, Oct. 1993, 25: 338-343.

* cited by examiner

IMMUNE GENE SIGNATURES IN UROTHELIAL CARCINOMA (UC)

This application is a National Stage application under 35 U.S.C. § 371 of International Application No. PCT/US2015/025288, filed Apr. 10, 2015, which claims the benefit of U.S. Provisional Patent Application Ser. No. 61/978,584, filed on Apr. 11, 2014. The entire contents of the foregoing are hereby incorporated by reference.

CLAIM OF PRIORITY

This application claims the benefit of U.S. Provisional Patent Application Ser. No. 61/978,584, filed on Apr. 11, 2014. The entire contents of the foregoing are hereby incorporated by reference.

FEDERALLY SPONSORED RESEARCH OR DEVELOPMENT

This invention was made with Government support under Grant No. CA148995 awarded by the National Institutes of Health. The Government has certain rights in the invention.

TECHNICAL FIELD

This invention relates to methods for identifying tumors associated with immune cell infiltration, and for making a prognosis, in subjects with urothelial carcinoma (UC).

BACKGROUND

Tumor-induced, host immune response has been described in breast (2-5), lung (6, 7), ovarian (8, 9), and CRC (10, 11) among other solid tumor types. This response may include fibrosis, lymphocytic or neutrophilic infiltration, and other reactive changes within the tumor and/or in the surrounding tissue.

Urothelial Cancer (UC) is one of several malignant neoplasm for which immunotherapy is often included as part of standard care. Intravesical application of the immunomodulator *Bacillus* Calmette-Guerin in patients with superficial (UC) reduces the risk of progression and local recurrence. Invasive UC elicit a brisk inflammatory response were higher prevalence of tumor infiltrating lymphocytes (TILs) is associated with a favorable response, even in the setting of a more invasive disease. In addition to the density of the lymphoid infiltrates the cellular composition was demonstrated to play a major role UC. Patients with higher numbers of CD8 TILs in stages pT2, pT3, and pT4 had better disease-free survival and overall survival compared to patients with similar-staged bladder cancers and fewer intratumoral CD8 TILs. Chemokines and their receptors are involved in malignant progression by establishing a microenvironment of immune cells that either suppress or induce specific antitumor responses. Hence, it is important to define the role of chemokines in tumor evolution and their potential use as prognostic or predictive biomarkers.

SUMMARY

The present invention is based, at least in part, on the discovery of gene signatures that predict the presence of infiltrating immune cells. Expression levels of these genes can be used to optimize or select treatment and predict survival in subjects with bladder cancer, e.g., with UC. As shown herein, a high score of 12-Chemokine GES is correlated with improved overall survival in stage IV patients with UC.

Thus, in a first aspect, the invention provides methods for predicting survival time for a subject who has a tumor of the bladder, e.g., UC. The methods include obtaining cells from the tumor; determining gene expression levels of chemokines CCL2, CCL3, CCL4, CCL5, CCL8, CCL18, CCL19, CCL21, CXCL9, CXCL10, CXCL11, and CXCL13 in the tumor cells; comparing the tumor gene expression levels to reference gene expression levels; and predicting longer survival time if tumor gene expression levels are above the reference gene expression levels, or predicting shorter survival time if tumor gene expression levels are below the reference gene expression levels.

In another aspect, the invention provides methods for monitoring an immunotherapy in a subject who has a tumor of the bladder, e.g., UC. The methods include obtaining cells from the tumor; determining first gene expression levels of chemokines CCL2, CCL3, CCL4, CCL5, CCL8, CCL18, CCL19, CCL21, CXCL9, CXCL10, CXCL11, and CXCL13 in the tumor cells; administering one or more doses of an immunotherapy to the subject; determining second gene expression levels of the same genes in the tumor cells; and comparing the first and second gene expression levels, wherein second gene expression levels that are higher than the first gene expression levels indicate that the treatment is effective, and second gene expression levels that are the same as or lower that the first gene expression levels indicate that the treatment is not effective.

In another aspect, the invention provides methods for treating a subject who has a tumor of the bladder, e.g., UC. The methods include obtaining cells from the tumor; determining gene expression levels of chemokines CCL2, CCL3, CCL4, CCL5, CCL8, CCL18, CCL19, CCL21, CXCL9, CXCL10, CXCL11, and CXCL13 in the tumor cells; comparing the tumor gene expression levels to reference gene expression levels; and selecting for the subject a treatment comprising an immunotherapy if tumor gene expression levels are above the reference gene expression levels, or selecting for the subject a treatment not comprising an immunotherapy if tumor gene expression levels are below the reference gene expression levels.

In a further aspect, the invention provides methods for selecting a treatment for a subject who has a tumor of the bladder, e.g., UC. The methods include obtaining cells from the tumor; determining gene expression levels of chemokines CCL2, CCL3, CCL4, CCL5, CCL8, CCL18, CCL19, CCL21, CXCL9, CXCL10, CXCL11, and CXCL13 in the tumor cells; comparing the tumor gene expression levels to reference gene expression levels; and selecting for the subject a treatment comprising an immunotherapy if tumor gene expression levels are above the reference gene expression levels, or selecting for the subject a treatment not comprising an immunotherapy if tumor gene expression levels are below the reference gene expression levels.

In some embodiments of the methods described herein, determining gene expression levels comprises determining protein levels. In some embodiments of the methods described herein, determining gene expression levels comprises determining mRNA levels.

In some embodiments of the methods described herein, the methods include determining chemokine gene expression levels. In some embodiments of the methods described herein, the methods include determining cytotoxic cell gene expression levels. In some embodiments of the methods described herein, the methods include determining dendritic cell gene expression levels. In some embodiments of the methods described herein, the methods include determining chemokine gene expression levels and cytotoxic cell gene expression levels. In some embodiments of the methods described herein, the methods include determining cytotoxic cell gene expression levels and dendritic cell gene expression levels. In some embodiments of the methods described herein, the methods include determining chemokine gene expression levels and dendritic cell gene expression levels. In some embodiments of the methods described herein, the methods include determining chemokine gene expression levels, cytotoxic cell gene expression levels, and dendritic cell gene expression levels.

In some embodiments of the methods described herein, the longer survival time is 2 years or more, e.g., 3 years or more, 4 years or more, or 5 years or more, and the shorter survival time is less than 2 years, e.g., less than 1 year, or less than 6 months.

In some embodiments of the methods described herein, the methods further include communicating predicted survival time to the subject or a health care provider. In some embodiments of the methods described herein, the methods further include communicating information regarding the effectiveness of a treatment to the subject or a health care provider. In some embodiments of the methods described herein, the methods further include communicating information regarding treatment or selection of a treatment to the subject or a health care provider.

In some embodiments of the methods described herein, immunotherapy comprises administering to the subject dendritic cells or peptides with adjuvant, a DNA-based vaccine, cytokines, cyclophosphamide, anti-interleukin-2R immunotoxin, or an anti-cancer antibody, e.g., an immune checkpoint blockade agent. In some embodiments, the antibody is anti-cluster of differentiation 137 (CD137), anti-Programmed cell death protein 1 (PD1), anti-Programmed death-ligand 1 (PDL1), or anti-cytotoxic T-lymphocyte-associated protein 4 (CTLA-4). In some embodiments, the immunotherapy comprises administering to the subject tumor-pulsed dendritic cells.

In some embodiments of the methods described herein, the subject is a human.

In some embodiments of the methods described herein, the cancerous tumor of the bladder is UC (also known as transitional cell carcinoma (TCC)), squamous cell carcinoma, or adenocarcinoma.

In some embodiments of the methods described herein, the methods include measuring expression levels of one or more of CD4, CD8, PDCD1, CTLA4, HER2, CSF2RB and TIM3, and comparing those levels to reference levels.

In some embodiments comparing gene expression levels comprises calculating an expression score based on the gene expression levels, e.g., based on the weighted average of the gene expression levels, and comparing the expression score to a reference expression score.

A "subject" as described herein can be any subject having a proliferative disorder. For example, the subject can be any mammal, such as a human, including a human cancer patient. Exemplary nonhuman mammals include a nonhuman primate (such as a monkey or ape), mouse, rat, goat, cattle, pig, horse, sheep, cat, and dog.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1A:
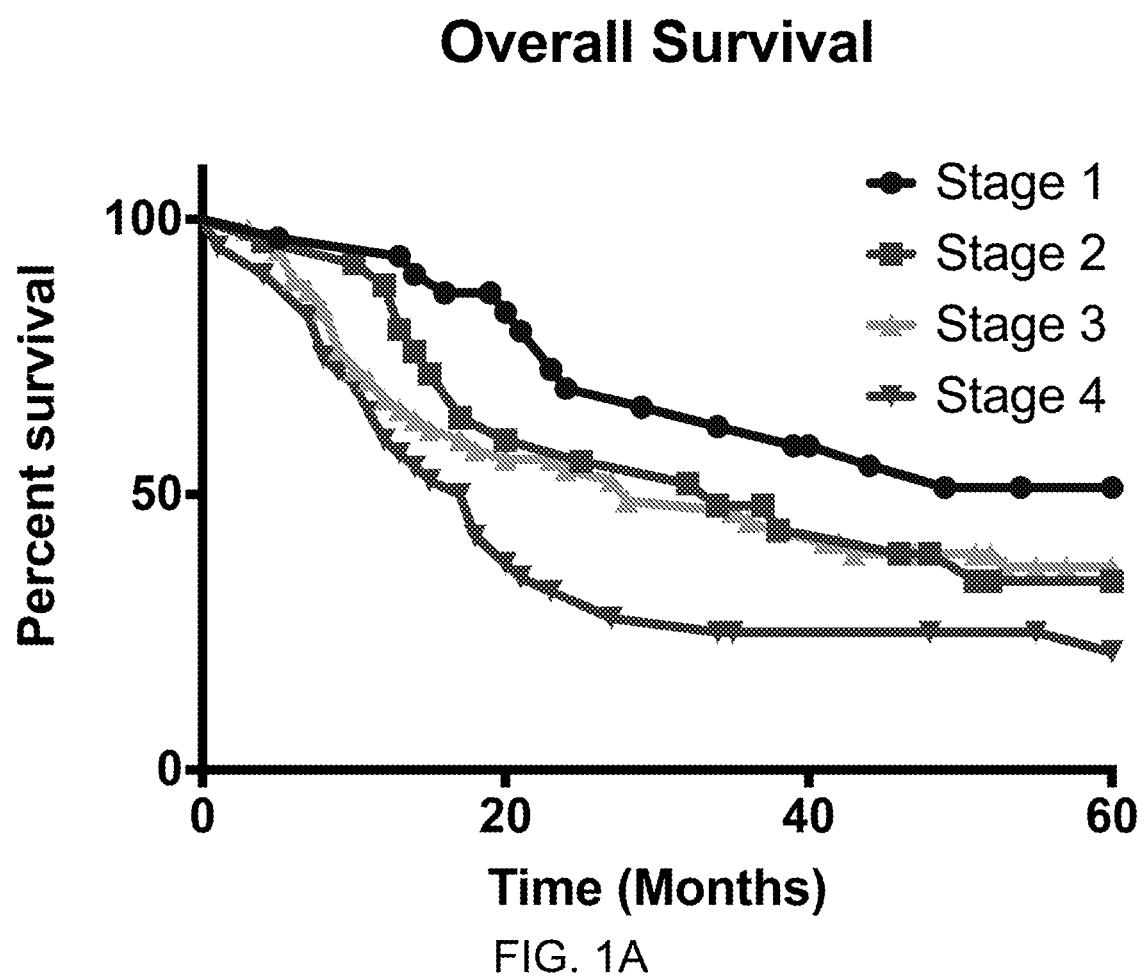
FIG. 1A is a graph showing overall survival correlated with disease stage.

It has been shown that some growing, human solid tumors are infiltrated by immune cells. Data characterizing the nature of this host immune response in a wide variety of distinct tumor types have been published in the recent literature (2-9), including primary CRCs (14). As shown herein, profiling gene signatures predicts the presence of infiltrating immune cells, and expression levels of these genes can be used to assign a prognosis and select or optimize treatment in subjects with tumors.

Methods of Assigning a Prognosis or Predicting Survival

The methods can be used to monitor a treatment (e.g., an immunotherapy), or to select a treatment, e.g., to select a treatment regime including an immunotherapy for a subject. In addition, the methods described herein can be used for, e.g., to assist in, assigning a prognosis or predicting survival in a subject who has a cancerous tumor of the bladder, e.g., UC (also known as Transitional cell carcinoma (TCC)), squamous cell carcinoma, or adenocarcinoma.

As used herein, the term "cancer" refers to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. In general, a cancer will be associated with the presence of one or more tumors, i.e., abnormal cell masses. The term "tumor" is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. In general, the methods described herein can be practiced on subjects with solid tumors.

Tumors include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the disease is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

In some embodiments, cancers evaluated and treated by the methods described herein include cancers of the bladder, e.g., UC (also known as transitional cell carcinoma (TCC)), squamous cell carcinoma, adenocarcinoma, or mixed.

presence of dendritic cell subpopulations, the level of which predicted better prognosis in some tumor types (7, 8, 22). A similar correlation was recently reported for patients with CRC (10).

Bladder Cancer

In some embodiments, the methods herein can be used to select treatment or predict survival in a subject who has a cancer of the bladder, e.g., UC (also known as transitional cell carcinoma (TCC)), squamous cell carcinoma, or adenocarcinoma.

Risk factors for development of urothelial carcinoma include age and exposure to environmental or industrial carcinogens, e.g., smoking or. Gross painless hematuria is the most common presentation; microscopic hematuria occurs in virtually all patients. Pain is a late feature indicating advanced disease. Bladder cancers are separated pathologically and clinically into superficial and invasive tumors. In some embodiments, the methods described herein are useful in invasive UC.

Assays, References, and Samples

The methods described herein include determining levels of selected chemokine genes. In some embodiments, all of the genes listed in the tables below are evaluated. In some embodiments, two, three, four, five, six, seven, eight, nine, ten, eleven, twelve, or more of the listed genes are evaluated. Although the terminology "genes" is used herein, in some embodiments, the methods include detecting levels of the proteins encoded by the listed genes. In some embodiments, the methods include detecting transcript (mRNA) levels.

Chemokines

Chemokines are secreted proteins involved in immunoregulatory and inflammatory processes. The chemokines used in the present methods are as follows:

| Chemokines | | | |
|---|---|---|---|
| Gene Symbol | Gene Name | GenBank Acc. No.: Nucleic Acid | GenBank Acc. No.: Protein |
| CCL2 | chemokine (C-C motif) ligand 2 | NM_002982.3 | NP_002973.1 |
| CCL3 | chemokine (C-C motif) ligand 3 | NM_002983.2 | NP_002974.1 |
| CCL4 | chemokine (C-C motif) ligand 4 | NM_002984.2 | NP_002975.1 |
| CCL5 | chemokine (C-C motif) ligand 5 | NM_002985.2 | NP_002976.2 |
| CCL8 | chemokine (C-C motif) ligand 8 | NM_005623.2 | NP_005614.2 |
| CCL18 | chemokine (C-C motif) ligand 18 (pulmonary and activation-regulated) | NM_002988.2 | NP_002979.1 |
| CCL19 | chemokine (C-C motif) ligand 19 | NM_006274.2 | NP_006265.1 |
| CCL21 | chemokine (C-C motif) ligand 21 | NM_002989.2 | NP_002980.1 |
| CXCL9 | chemokine (C-X-C motif) ligand 9 | NM_002416.1 | NP_002407.1 |
| CXCL10 | chemokine (C-X-C motif) ligand 10 | NM_001565.2 | NP_001556.2 |
| CXCL11 | chemokine (C-X-C motif) ligand 11 | NM_005409.4 | NP_005400.1 |
| CXCL13 | chemokine (C-X-C motif) ligand 13 | NM_006419.2 | NP_006410.1 |

In some embodiments, the subject has stage 4 bladder cancer; see, e.g., AJCC: Urinary bladder. In: Edge S B, Byrd D R, Compton C C, et al., eds.: AJCC Cancer Staging Manual. 7th ed. New York, N.Y.: Springer, 2010, pp 497-505, or Edge S B, Byrd D R, Compton C C, et al., eds.: AJCC Cancer Staging Manual. 7th ed. New York, N.Y.: Springer, 2010, p 497.

Lymphoid Structures in Solid Tumors

Lymphoid structures have been described in solid tumors. As examples, Coronella-Wood et al. (2, 3) have described breast tumor-infiltrating lymphocytes composed of B cell aggregates containing interdigitating CD21+ follicular dendritic cells. The presence of ectopic, organized lymphoid tissue has also been reported in ovarian (8, 9, 19); colon (20, 21); and lung tumors (6, 7), which has mostly focused on the In some embodiments, the methods include assaying the presence or levels of chemokine mRNA or proteins in the sample. The presence and/or level of a protein can be evaluated using methods known in the art, e.g., using quantitative immunoassay methods. The presence and/or level of an mRNA can be evaluated using methods known in the art, e.g., Northern blotting or quantitative PCR methods, e.g., RT-PCR. In some embodiments, high throughput methods, e.g., protein or gene chips as are known in the art (see, e.g., Ch. 12, Genomics, in Griffiths et al., Eds. Modern genetic Analysis, 1999, W. H. Freeman and Company; Ekins and Chu, Trends in Biotechnology, 1999, 17:217-218; MacBeath and Schreiber, Science 2000, 289(5485):1760-1763; Simpson, *Proteins and Proteomics: A Laboratory Manual*, Cold Spring Harbor Laboratory Press; 2002; Hardiman,

*Microarrays Methods and Applications: Nuts & Bolts*, DNA Press, 2003), can be used to detect the presence and/or level of chemokine proteins as described herein.

In some embodiments, the methods include assaying levels of one or more control genes or proteins, and comparing the level of expression of the chemokine genes or proteins to the level of the control genes or proteins, to normalize the levels of the chemokine genes or proteins. Suitable endogenous control genes includes a gene whose expression level should not differ between samples, such as a housekeeping or maintenance gene, e.g., 18S ribosomal RNA; beta Actin; Glyceraldehyde-3-phosphate dehydrogenase; Phosphoglycerate kinase 1; Peptidylprolyl isomerase A (cyclophilin A); Ribosomal protein L13a; large Ribosomal protein P0; Beta-2-microglobulin; Tyrosine 3-monooxygenase/tryptophan 5-monooxygenase activation protein, zeta polypeptide; Succinate dehydrogenase; Transferrin receptor (p90, CD71); Aminolevulinate, delta-, synthase 1; Glucuronidase, beta; Hydroxymethyl-bilane synthase; Hypoxanthine phosphoribosyltransferase 1; TATA box binding protein; and/or Tubulin, beta polypeptide.

Generally speaking, the methods described herein can be performed on cells from a tumor. The cells can be obtained by known methods, e.g., during a biopsy (such as a core needle biopsy or cystoscopic biopsy), or during a surgical procedure to remove all or part of the tumor (e.g., transurethral resection of the bladder tumor (TURBT), or partial or radical (complete) cystectomy). The cells can be used fresh, frozen, fixed, and/or preserved, so long as the mRNA or protein that is to be assayed is maintained in a sufficiently intact state to allow accurate analysis.

In some embodiments of the methods described herein, the levels of the chemokine genes in the tumor sample can be compared individually to levels in a reference. The reference levels can represent levels in a subject who has a good prognosis, or a long predicted survival time (e.g., 2 years or more). Alternatively, reference levels can represent levels in a subject who has a poor prognosis, or a shorter predicted survival time (e.g., less than 2 years). In some embodiments, the reference levels represent a threshold, and a level in the tumor that is above the threshold reference level indicates that the subject has a good prognosis, or a long predicted survival time (e.g., 2 years or more), and levels below the threshold reference level indicates that the subject has a poor prognosis, or a shorter predicted survival time (e.g., less than 2 years).

In some embodiments, the reference levels can represent levels in a subject who has lymphoid like structures present in the tumor, or is predicted to respond to immunotherapy. Alternatively, reference levels can represent levels in a subject who lacks tumor lymphoid structures, or is predicted to have no or a poor response to immunotherapy. In some embodiments, the reference levels represent a threshold, and a level in the tumor that is above the threshold reference level indicates that the subject has tumor lymphoid structures, or is predicted to respond to immunotherapy, and levels below the threshold reference level indicates that the subject lacks lymphoid structures and is predicted to have no or poor response to immunotherapy. In subjects who are predicted to have tumor lymphoid structures, or who are predicted to respond to immunotherapy, the methods can further include administering an immunotherapy for those subjects, or selecting or recommending a treatment including an immunotherapy for those subjects.

In some embodiments of the methods described herein, values representing the levels of the chemokine genes can be summed to produce a "tumor chemokine gene score" that can be compared to a reference chemokine gene score, wherein a tumor chemokine gene score that is above the reference chemokine gene score indicates that the subject has a long predicted survival time (e.g., 2 years or more) or is predicted to have a positive response to immunotherapy, and a chemokine gene score below the reference score indicates that the subject has a shorter predicted survival time (e.g., less than 2 years), or is predicted to have no or a poor response to immunotherapy.

For example, in some embodiments, the expression levels of each of the evaluated genes can be assigned a value (e.g., a value that represents the expression level of the gene, e.g., normalized to an endogenous control gene as described herein). That value (optionally weighted to increase or decrease its effect on the final score) can be summed to produce a chemokine gene score. One of skill in the art could optimize such a method to determine an optimal algorithm for determining a chemokine gene score.

The methods described herein can include determining levels (or scores) for all of the 12 chemokine genes. In some embodiments all of the genes in each set are evaluated, but in some embodiments a subset of one or all of the sets is evaluated.

One of skill in the art will appreciate that references can be determined using known epidemiological and statistical methods, e.g., by determining a chemokine gene score, or chemokine gene protein or mRNA levels, in tumors from an appropriate cohort of subjects, e.g., subjects with the same type of cancer as the test subject and a known prognosis (e.g., good or poor) or predicted survival time (e.g., less than 2 years, or 2 years or more).

In some embodiments, the methods include selecting and optionally administering treatment, e.g., an immunotherapy, e.g., comprising administering to the subject therapies that promote anti-cancer immunity, including administering one or more of: dendritic cells or peptides with adjuvant, DNA-based vaccines, cytokines (e.g., IL-2), cyclophosphamide, anti-interleukin-2R immunotoxins, and/or antibodies (e g, immune checkpoint blockage agents) such as anti-CD137 (BMS-663513), anti-PD1 (e.g., (nivolumab, see Topalian, et al., NEJM. 366(26): 2443-2454 (2012) and WO2013/173223A1, pembrolizumab/MK-3475, Pidilizumab (CT-011)), anti-PDL1 (e.g., BMS-936559, MPDL3280A), or anti-CTLA-4 (e.g., ipilimumab, see Tarhini and Iqbal, Onco Targets Ther. 3:15-25 (2010) and U.S. Pat. No. 7,741,345 or Tremelimumab); see, e.g., Powles et al., "MPDL3280A (anti-PD-L1) treatment leads to clinical activity in metastatic bladder cancer," Nature. 2014 Nov. 27; 515(7528):558-62, Kruger et al., "Immune based therapies in cancer," Histol Histopathol. 2007 Jun; 22(6):687-96; Eggermont et al., "Anti-CTLA-4 antibody adjuvant therapy in melanoma," Semin Oncol. 2010 Oct; 37(5):455-9; Klinke D J 2nd, "A multiscale systems perspective on cancer, immunotherapy, and Interleukin-12," Mol Cancer. 2010 Sep. 15; 9:242; Alexandrescu et al., "Immunotherapy for melanoma: current status and perspectives," J Immunother. 2010 Jul-Aug; 33(6):570-90; Moschella et al., "Combination strategies for enhancing the efficacy of immunotherapy in cancer patients," Ann N Y Acad Sci. 2010 Apr; 1194:169-78; Ganesan and Bakhshi, "Systemic therapy for melanoma," Natl Med J India. 2010 Jan-Feb; 23(1):21-7; Golovina and Vonderheide, "Regulatory T cells: overcoming suppression of T-cell immunity," Cancer J. 2010 Jul-Aug; 16(4):342-7. In some embodiments, the methods include administering a composition comprising tumor-pulsed dendritic cells, e.g., as described in WO2009/114547 and references cited therein. See also Shiao et al., Genes & Dev. 2011. 25: 2559-2572.

In some embodiments, the methods can be used to monitor the efficacy of a treatment, e.g., an immunotherapy. The methods include determining levels of the chemokine genes in a sample, then administering one or more doses of the treatment, then determining levels of the chemokine genes to determine whether the treatment has increase immune infiltration of the tumor. An increase in chemokine gene levels (or chemokine gene score, if calculated) indicates that the treatment was effective.

Computer Software/Hardware

Standard computing devices and systems can be used and implemented to perform the methods described herein. Computing devices include various forms of digital computers, such as laptops, desktops, mobile devices, workstations, personal digital assistants, servers, blade servers, mainframes, and other appropriate computers. In some embodiments, the computing device is a mobile device, such as personal digital assistant, cellular telephone, smartphone, tablet, or other similar computing device. The components described herein, their connections and relationships, and their functions, are meant to be exemplary only, and are not meant to limit implementations of the inventions described and/or claimed in this document.

Computing devices typically include one or more of a processor, memory, a storage device, a high-speed interface connecting to memory and high-speed expansion ports, and a low speed interface connecting to low speed bus and storage device. Each of the components are interconnected using various busses, and can be mounted on a common motherboard or in other manners as appropriate. The processor can process instructions for execution within the computing device, including instructions stored in the memory or on the storage device to display graphical information for a GUI on an external input/output device, such as a display coupled to a high speed interface. In other implementations, multiple processors and/or multiple buses can be used, as appropriate, along with multiple memories and types of memory. Also, multiple computing devices can be connected, with each device providing portions of the operations (e.g., as a server bank, a group of blade servers, or a multi-processor system).

The memory stores information within the computing device. In some embodiments, the memory is a computer-readable medium. In one implementation, the memory is a volatile memory unit or units. In another implementation, the memory is a non-volatile memory unit or units.

The storage device is capable of providing mass storage for the computing device. In one implementation, the storage device is a computer-readable medium. In various different implementations, the storage device can be a floppy disk device, a hard disk device, an optical disk device, or a tape device, a flash memory or other similar solid state memory device, or an array of devices, including devices in a storage area network or other configurations. In one implementation, a computer program product is tangibly embodied in an information carrier. The computer program product contains instructions that, when executed, perform one or more methods, such as those described above. The information carrier is a computer- or machine-readable medium, such as the memory, the storage device, memory on processor, or a propagated signal.

The high speed controller manages bandwidth-intensive operations for the computing device, while the low speed controller manages lower bandwidth-intensive operations. Such allocation of duties is exemplary only. In one implementation, the high-speed controller is coupled to memory, the display (e.g., through a graphics processor or accelerator), and to high-speed expansion ports, which can accept various expansion cards (not shown). In the implementation, the low-speed controller is coupled to a storage device and low-speed expansion port. The low-speed expansion port, which can include various communication ports (e.g., USB, Bluetooth, Ethernet, wireless Ethernet) can be coupled to one or more input/output devices, such as a keyboard, a pointing device, a scanner, or a networking device such as a switch or router, e.g., through a network adapter.

The computing device can be implemented in a number of different forms. For example, it can be implemented as a standard server, or multiple times in a group of such servers. It can also be implemented as part of a rack server system. In addition, it can be implemented in a personal computer such as a laptop computer. Alternatively, components from the computing device can be combined with other components in a mobile device. Each of such devices can contain one or more computing devices, and an entire system can be made up of multiple computing devices communicating with each other.

The computing device typically includes a processor, memory, an input/output device such as a display, a communication interface, and a transceiver, among other components. The device can also be provided with a storage device, such as a microdrive or other device, to provide additional storage. Each of these components are interconnected using various buses, and several of the components can be mounted on a common motherboard or in other manners as appropriate.

The processor can process instructions for execution within the computing device, including instructions stored in the memory. The processor can also include separate analog and digital processors. The processor can provide, for example, for coordination of the other components of the device, such as control of user interfaces, applications run by the device, and wireless communication by the device.

The processor can communicate with a user through control interface and display interface coupled to a display. The display can be, for example, a TFT LCD display or an OLED display, or other appropriate display technology. The display interface can comprise appropriate circuitry for driving the display to present graphical and other information to a user. The control interface can receive commands from a user and convert them for submission to the processor. In addition, an external interface can be provide in communication with the processor, so as to enable near area communication of device with other devices. External interface can provide, for example, for wired communication (e.g., via a docking procedure) or for wireless communication (e.g., via Bluetooth or other such technologies).

The memory stores information within the computing device. In one implementation, the memory is a computer-readable medium. In one implementation, the memory is a volatile memory unit or units. In another implementation, the memory is a non-volatile memory unit or units. Expansion memory can also be provided and connected to the device through an expansion interface, which can include, for example, a SIMM card interface. Such expansion memory can provide extra storage space for device, or can also store applications or other information for the device. Specifically, expansion memory can include instructions to carry out or supplement the processes described above, and can include secure information also. Thus, for example, expansion memory can be provided as a security module for the device, and can be programmed with instructions that permit secure use of the device. In addition, secure applications can be provided via the SIMM cards, along with additional information, such as placing identifying information on the SIMM card in a non-hackable manner.

The memory can include for example, flash memory and/or MRAM memory, as discussed below. In one implementation, a computer program product is tangibly embodied in an information carrier. The computer program product contains instructions that, when executed, perform one or more methods, such as those described above. The information carrier is a computer- or machine-readable medium, such as memory, expansion memory, memory on processor, or a propagated signal.

The device can communicate wirelessly through a communication interface, which can include digital signal processing circuitry where necessary. The communication interface can provide for communications under various modes or protocols, such as GSM voice calls, SMS, EMS, or MMS messaging, CDMA, TDMA, PDC, WCDMA, CDMA2000, or GPRS, among others. Such communication can occur, for example, through a radio-frequency transceiver. In addition, short-range communication can occur, such as using a Bluetooth, WiFi, or other such transceiver.

The device can also communication audibly using audio codec, which can receive spoken information from a user and convert it to usable digital information. Audio codex can likewise generate audible sound for a user, such as through a speaker, e.g., in a handset of device. Such sound can include sound from voice telephone calls, can include recorded sound (e.g., voice messages, music files, etc.) and can also include sound generated by applications operating on device.

The computing device can be implemented in a number of different forms, as shown in the figure. For example, it can be implemented as a cellular telephone. It can also be implemented as part of a smartphone, tablet, personal digital assistant, or other similar mobile device.

Where appropriate, the systems and the functional operations described in this specification can be implemented in digital electronic circuitry, or in computer software, firmware, or hardware, including the structural means disclosed in this specification and structural equivalents thereof, or in combinations of them. The techniques can be implemented as one or more computer program products, i.e., one or more computer programs tangibly embodied in an information carrier, e.g., in a machine readable storage device or in a propagated signal, for execution by, or to control the operation of, data processing apparatus, e.g., a programmable processor, a computer, or multiple computers. A computer program (also known as a program, software, software application, or code) can be written in any form of programming language, including compiled or interpreted languages, and it can be deployed in any form, including as a standalone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub programs, or portions of code). A computer program can be deployed to be executed on one computer or on multiple computers at one site or distributed across multiple sites and interconnected by a communication network.

The processes and logic flows described in this specification can be performed by one or more programmable processors executing one or more computer programs to perform the described functions by operating on input data and generating output. The processes and logic flows can also be performed by, and apparatus can be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, the processor will receive instructions and data from a read only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. Information carriers suitable for embodying computer program instructions and data include all forms of non volatile memory, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, aspects of the described techniques can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The techniques can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation, or any combination of such back-end, middleware, or front-end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

One computer-implemented modeling algorithm is described herein (namely, principal component analysis (PCA)), although such algorithms themselves are generally outside the scope of the present invention. Other software-based modeling algorithms can also be utilized, alone or in combination, such as classification or decision trees, elastic net analysis, linear and polynomial support vector machines (SMV), shrunken centroids, random forest algorithms, support vector machines or neural networks.

EXAMPLES

The invention is further described in the following examples, which do not limit the scope of the invention described in the claims.

Example 1

A 12-chemokine gene expression signature (GES) was previously shown to correlate with better patient prognosis in colorectal carcinomas and metastatic melanomas. This study examines the relationship of the previously established 12-chemokine GES to overall survival in 150 patients with T1-T4 Urothelial Carcinoma (UC).

Tumor specimens from 150 patients at various stages treated with for urinary bladder TCC were examined by mRNA microarray analysis. All 150 patients were enrolled in the Moffitt TOTAL CANCER CARE protocol with appropriate consent. Analysis was performed on deidentified data. The tumor tissue was arrayed on a custom Affymetrix GENECHIP microarray. The expression data for the 150 individual patients was normalized using IRON (Welsh et al., BMC Bioinformatics. 2013;14(1):153) and expression data, in log2 units, for the 12 chemokine genes (CCL2, CCL3, CCL4, CCL5, CCL8, CCL18, CCL19, CCL21, CXCL9, CXCL10, CXCL11, and CXCL13, represented in 13 probesets) were extracted, with the following probes:

| Probeset | GeneSymbol |
|---|---|
| merck-NM__002988_at | CCL18 |
| merck-NM__006274_at | CCL19 |
| merck-NM__002982_at | CCL2 |
| merck-NM__002989_at | CCL21 |
| merck-D63785_x_at | CCL3 |
| merck-NM__002984_at | CCL4 |
| merck-NM__002985_at | CCL5 |
| merck-NM__005623_at | CCL8 |
| merck-NM__001565_at | CXCL10 |
| merck-NM__005409_at | CXCL11 |
| merck2-NM__005409_at | CXCL11 |
| merck-NM__006419_at | CXCL13 |
| merck-NM__002416_at | CXCL9 |

A 12-Chemokine GES was identified previously in colorectal cancer from a metagene grouping with overwhelming enrichment for immune-related and inflammation-related genes (see WO 2011/094483).

A principal component analysis (PCA) was performed from these 13 probe sets. Principal component analysis (PCA) is a technique that reduces a high-dimensional dataset to a low-dimensional dataset while retaining most of the variation in the data (Jolliffe IT. Principal Component Analysis. 2ed. New York: Springer; 2002). The new low-dimensional dataset is created by the PCA-derived principal components also called scores. These are a linear combination of all variables, where the loadings describe the importance of the original variable for each principal component. The first principal component describes most of the variance and is often considered the most important principal component, while the following principal components shows a decreasing amount of explained variance. The results of a PCA models are frequently visualized in score and loading plots. The score plot is related to the samples and shows which samples are similar to each other, groupings between classes of samples and also outliers. The loading plot shows which variables are important for the results seen in the score plot and also which variables are similar to each other. PCA was performed using EVINCE analysis software V2.5.5 (UmBio AB, Umeå, Sweden). Each variable was normalized to unit variance prior to PCA. PC1, representing the most variability (~58.5%) within the samples, was used to represent the chemokine signature. Based on PC1, samples with values above or below the median were identified as the high and low expressers of the chemokine signature, respectively.

| PCA Analysis of 150 subjects with bladder cancer | | | | |
|---|---|---|---|---|
| GeneSymbol | Probeset | Scaling Weight | Mean | PC1 Loading (p[1]) |
| CCL18 | merck-NM__002988_at | 0.5578 | 9.7346 | 0.2631 |
| CCL19 | merck-NM__006274_at | 0.5503 | 7.6328 | 0.1869 |
| CCL2 | merck-NM__002982_at | 0.7258 | 10.0320 | 0.2301 |
| CCL21 | merck-NM__002989_at | 0.4938 | 8.5706 | 0.1709 |
| CCL3 | merck-D63785_x_at | 0.7824 | 6.7552 | 0.2424 |
| CCL4 | merck-NM__002984_at | 0.8081 | 8.8762 | 0.3076 |
| CCL5 | merck-NM__002985_at | 0.7415 | 9.3045 | 0.2995 |
| CCL8 | merck-NM__005623_at | 0.6446 | 8.4278 | 0.2895 |
| CXCL10 | merck-NM__001565_at | 0.4716 | 8.6890 | 0.3239 |
| CXCL11 | merck-NM__005409_at | 0.4313 | 6.8438 | 0.3094 |
| CXCL11 | merck2-NM__005409_at | 0.4507 | 5.9064 | 0.3133 |
| CXCL13 | merck-NM__006419_at | 0.4674 | 7.9800 | 0.2875 |
| CXCL9 | merck-NM__002416_at | 0.4627 | 8.5950 | 0.3245 |

The 12-chemokine score for bladder tumors was also compared to other cancer types. Survival analysis was performed using KM-plots and statistical significance was assessed using a log rank test. High and low signature score was determined by median PCA score.

Figure 1B:
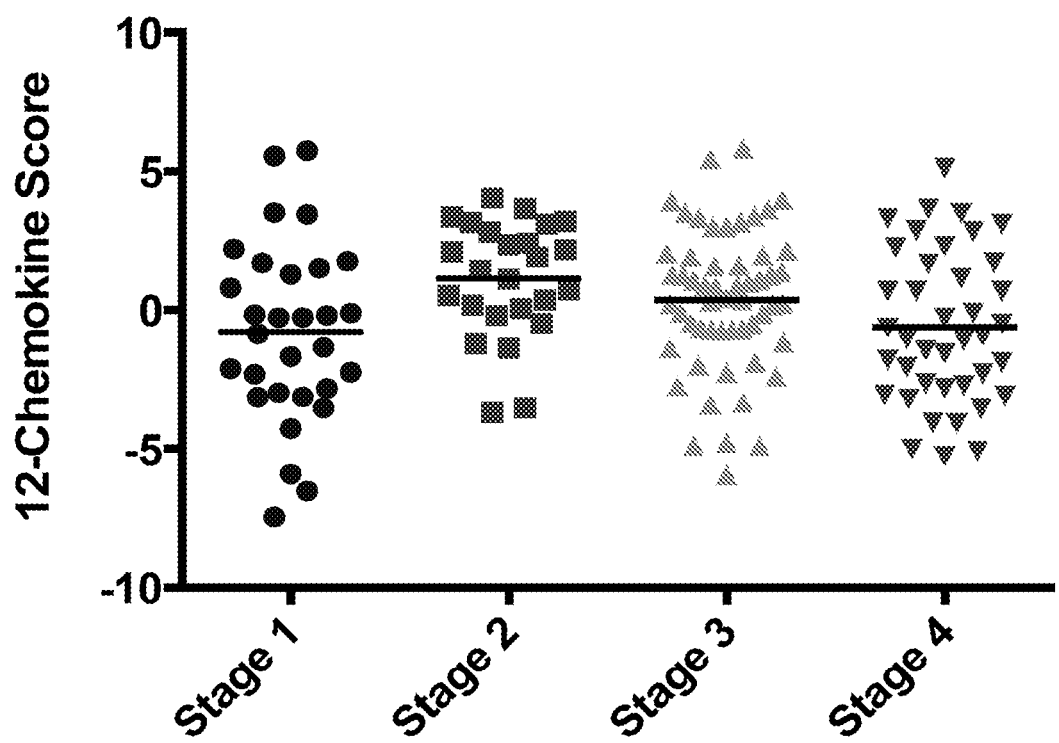
FIG. 1B is a graph showing a 12-Chemokine gene expression signature (GES) in UC. The tumors were staged in T1-T4 (T1: 30, T2: 25, T3: 55 and T4:40). There was no clear difference in 12-Chemokine GES between the stages as shown to the left.

The tumors were staged in T1-T4 (T1: 30, T2: 25, T3: 55 and T4:40). 15 of the 30 stage 1 patients had been treated with immunotherapy. FIG. 1A illustrates the significant difference in survival between the stages (as expected). As shown in FIG. 1B, there was no clear difference in 12-Chemokine GES between the stages.

Figure 2A:
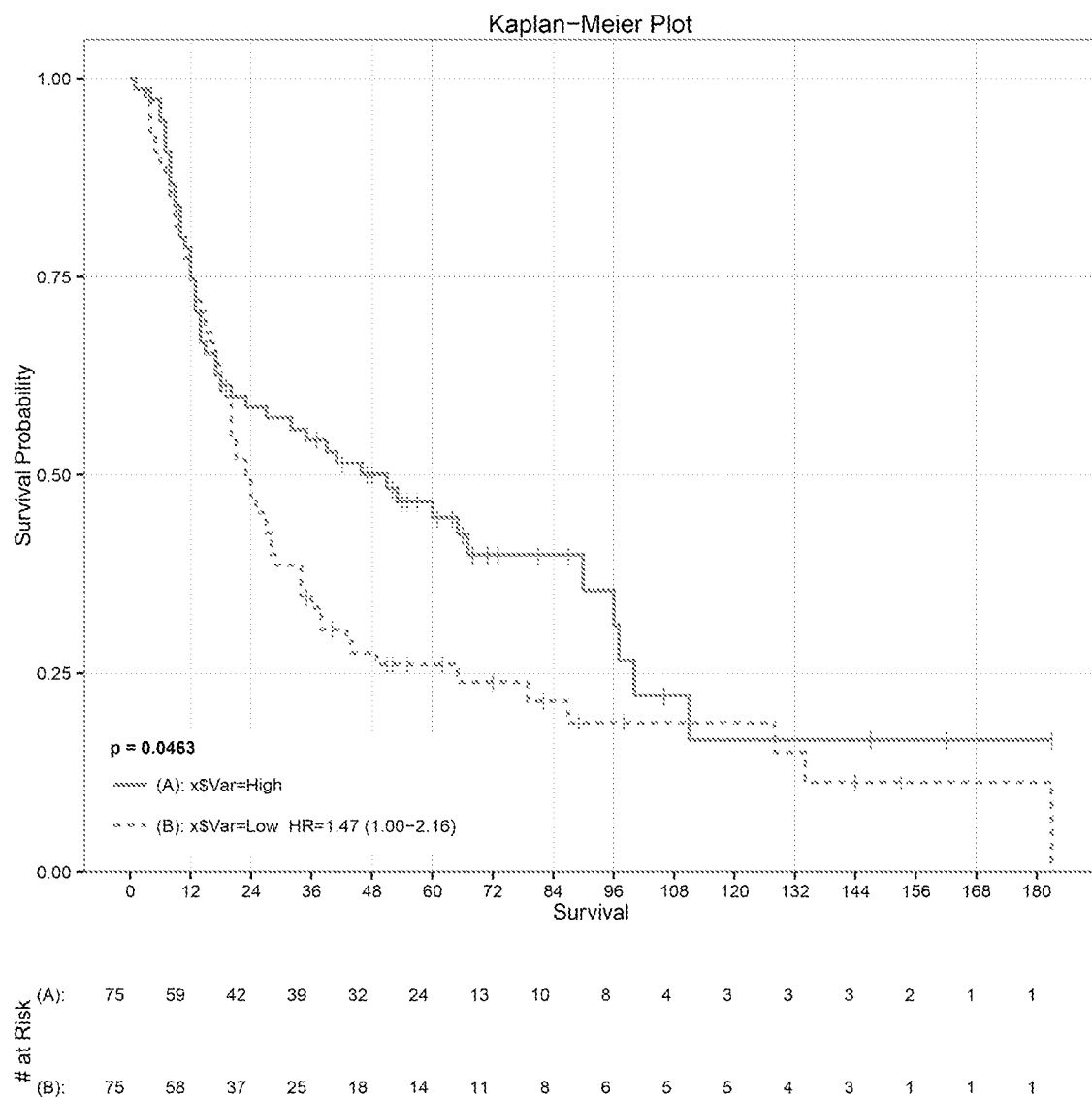
FIG. 2A is a Kaplan-Meier survival plot showing correlation of survival with high versus low levels of the GES. The median cut value for the 12-Chemokine score was 0.1831, with a Log rank p=0.0463 and Cox p=0.056.
Figure 2B:
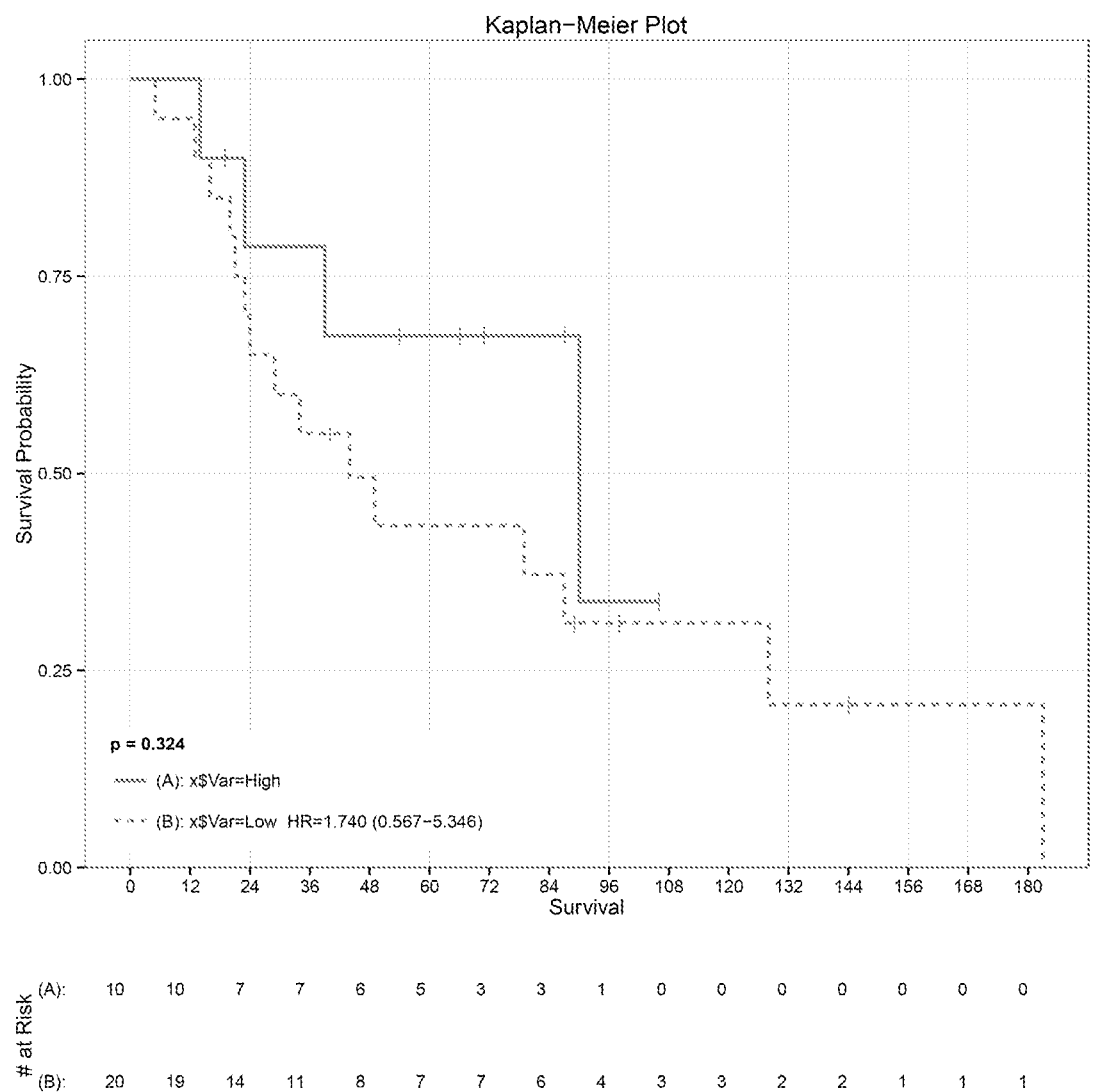
FIGS. 2B-E are Kaplan-Meier survival plot showing correlation of survival with high versus low levels of the GES in subjects with stage 1 (2B), stage 2 (2C), stage 3 (2D) and stage 4 (2E) disease.
Figure 2C:
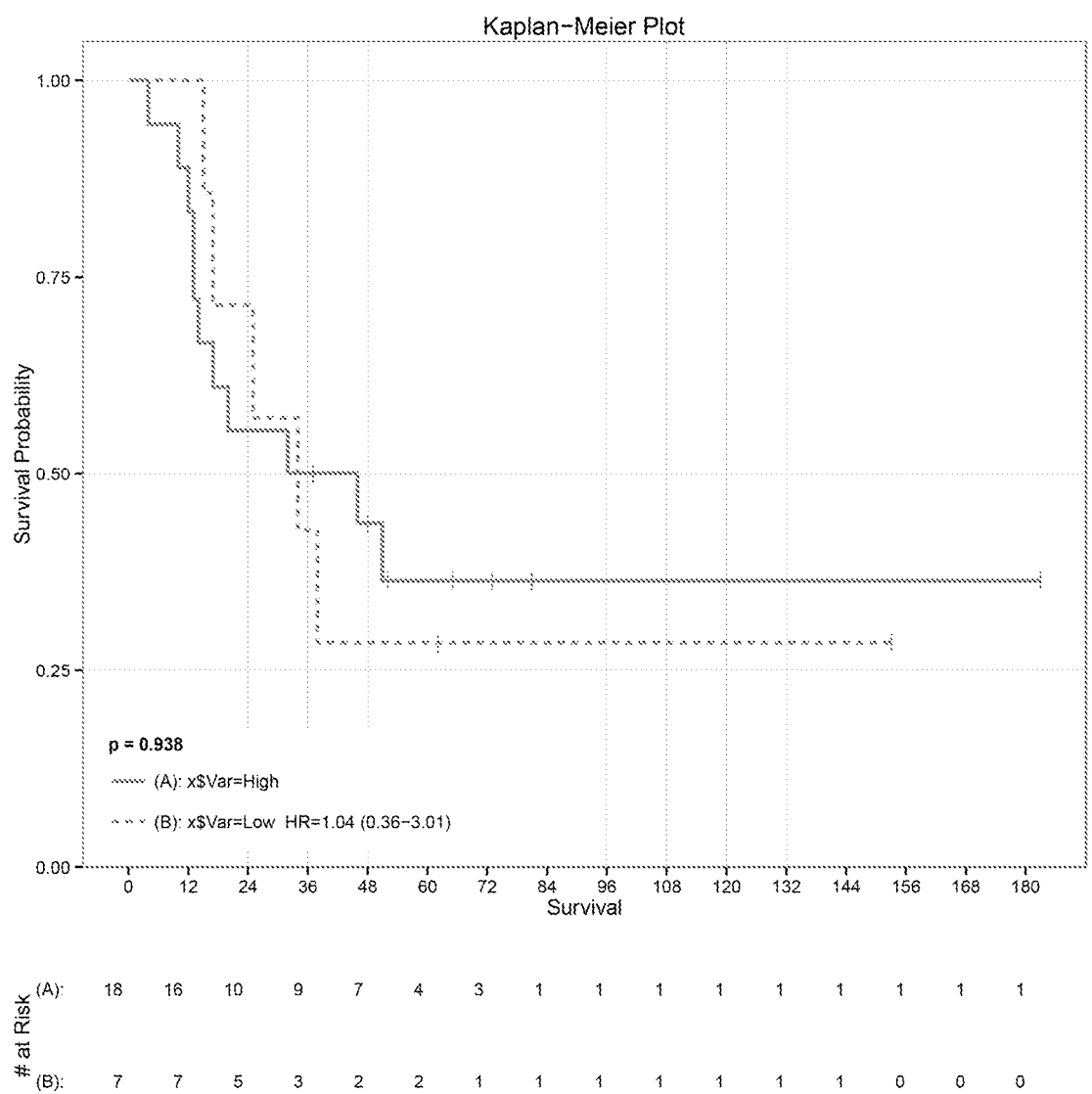
Figure 2D:
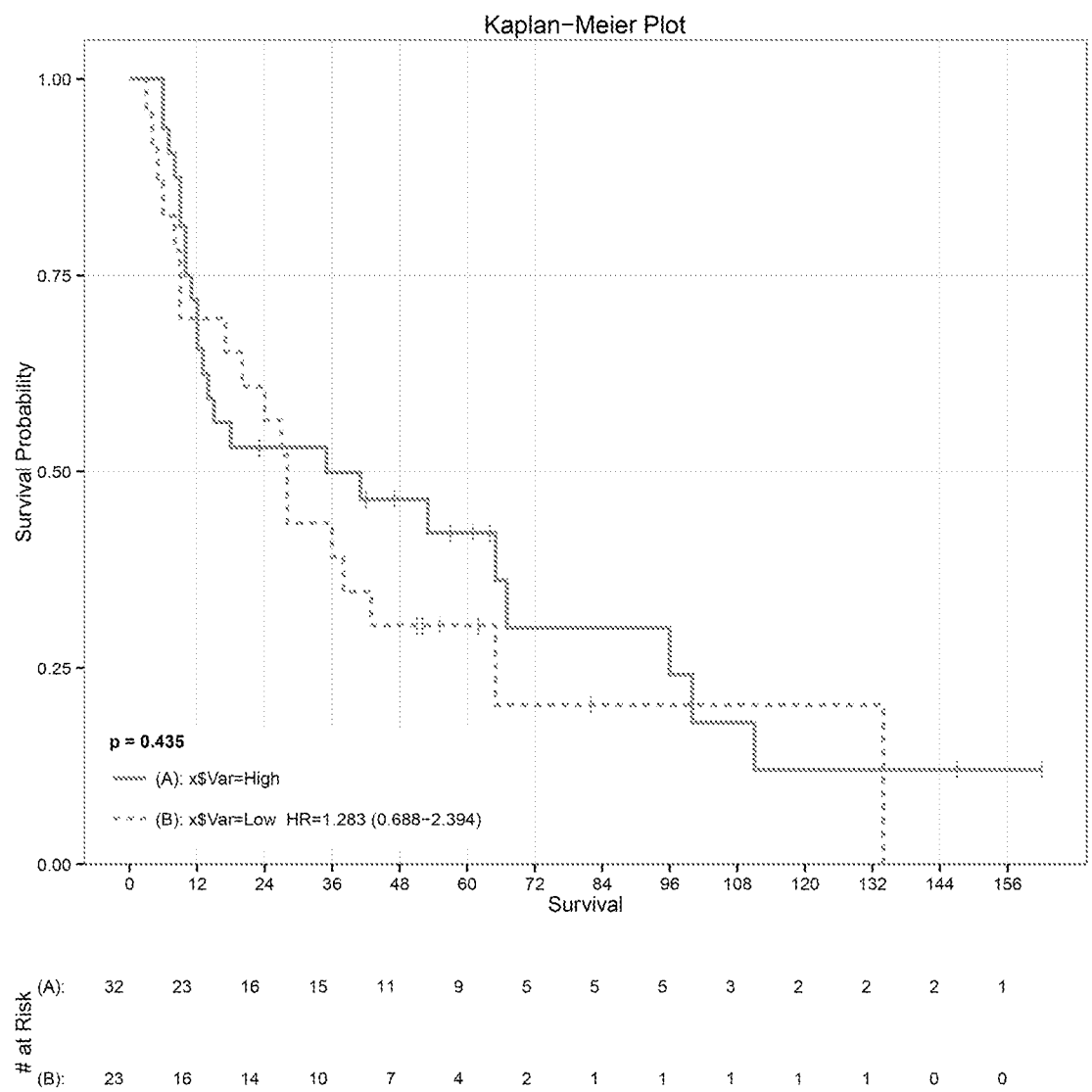
Figure 2E:
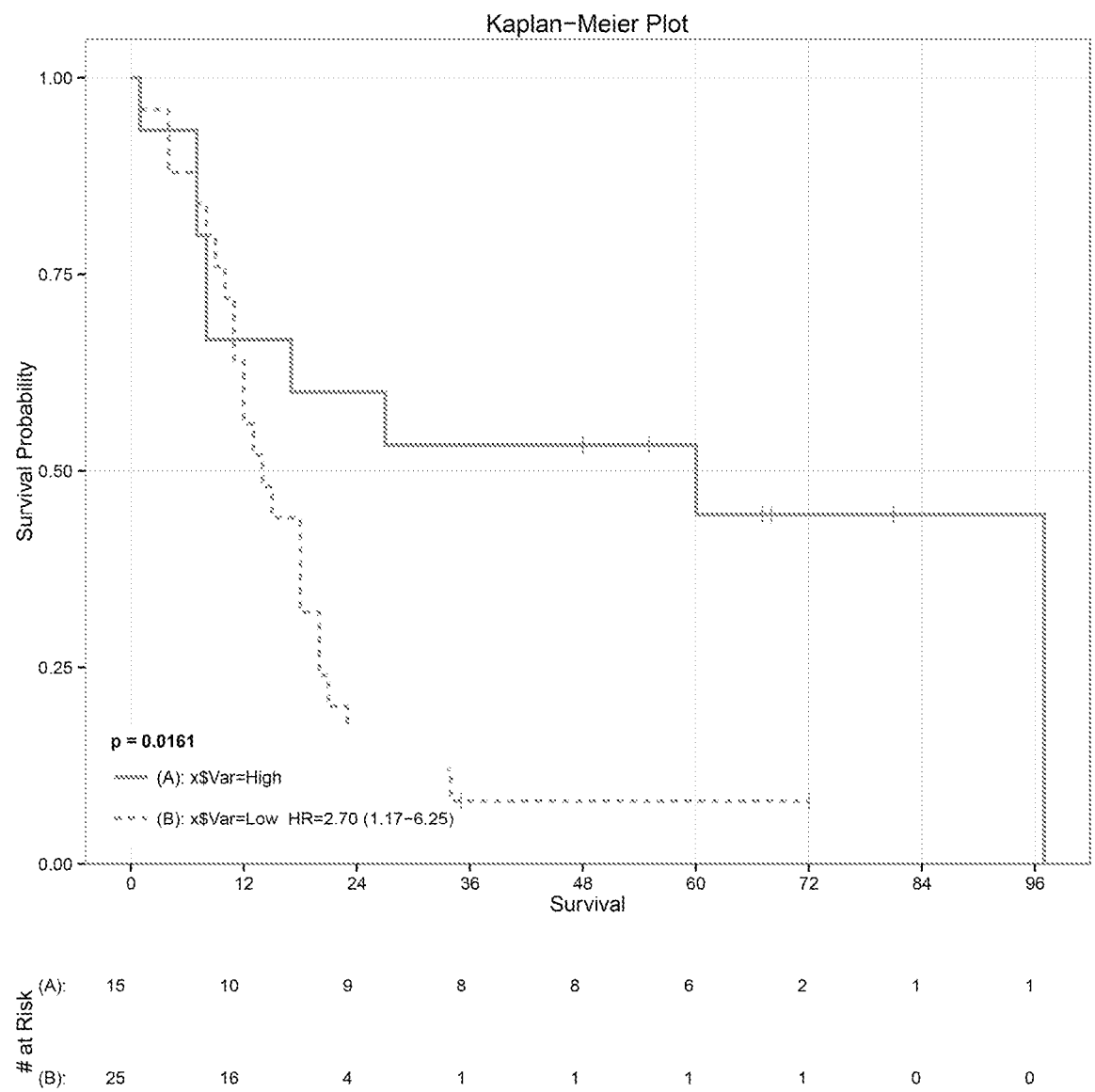

As shown in FIG. 2A, high expression of the 12-Chemokine GES was correlated with improved overall survival in with bladder cancer. This finding is in agreement with previously described finding in colorectal carcinoma and lung cancer, both tumor associated with dense inflammatory response. In CRC high expression of genes encoding for chemokines CX3CL1, CXCL9 and CXCL10 was associated with the infiltration of memory T cells and effector T cells, particularly Th1 cells, and was associated with prolonged disease-free survival and overall survival (see WO 2011/094483). The 12-chemokine score survival analysis was significant for stage 4 patients, as shown in FIGS. 2B-E.

Figure 3A:
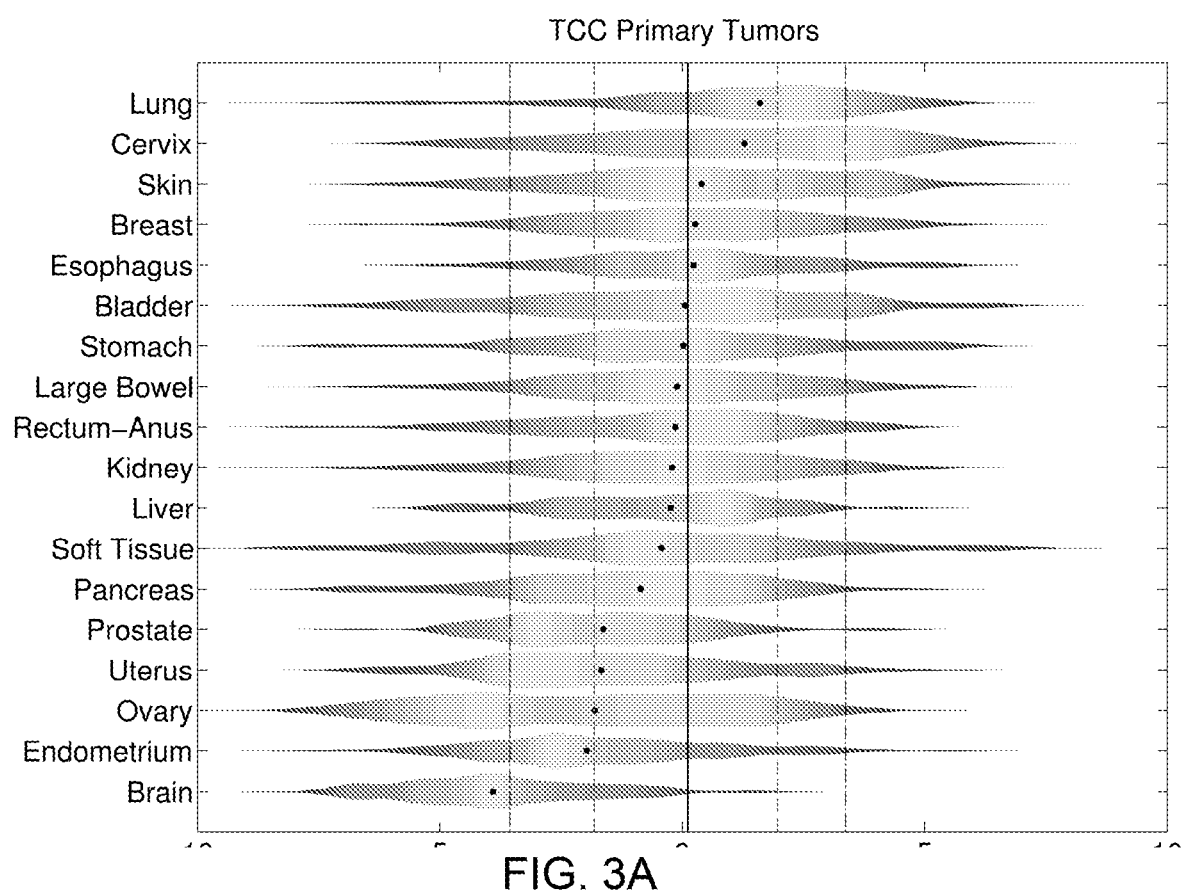
FIG. 3A is a graph showing that the 12-Chemokine GES for bladder tumors showed a large range with many scoring as high as lung and skin (melanoma) samples.
Figure 3B:
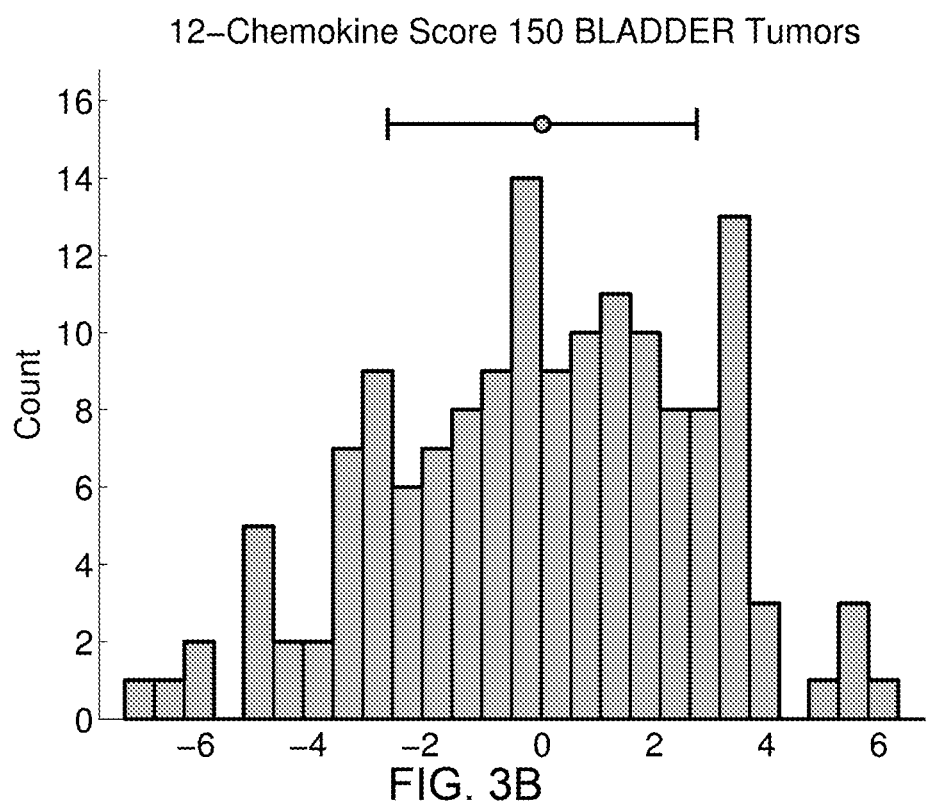
FIG. 3B is a graph of the 12-Chemokine distribution in 150 Bladder cancer samples.

As shown in FIG. 3A, the 12-Chemokine GES for bladder tumors showed a large range with many scoring as high as lung and skin (melanoma) samples. There were 5 samples showing a large 12-Chemokine immune score (above +4) and 4 with a low score (−6 or below, see FIG. 3B).

By Cox regression analysis, Stage alone was correlated with survival (p=0.006; b=0.310, (se=0.0952), but Stage plus the 12-Chemokine Score was correlated with greater significance (p=0.0008, 0.027; b=0.3155, −0.0763 (se=0.0944, 0.0345); the model was improved by inclusion of the 12-Chemokine Score (p=0.0278).

Additional markers were analyzed for their effect on the model; their correlation to the 12-chemokine score and survival analysis was determined. CD3e, CD4, CD8, PDCD1, CTLA4, and TIM3, correlated with 12-Chemokine signature, both in TCC and in bladder, while GM-CSF (CSF2) was not. CTLA4 was also correlated with overall survival. HER2, which was highly expressed in bladder cancers, was not related to overall survival but was significant for Stage 4 survival (though not by Cox regression). CD3e, CD4, CD8, STAT3, and PRKCB were not correlated with overall survival. CSF2RB expression was correlated with the 12-Chemokine signature, but was only significant for survival in Stage 3 patients.

Figure 4A:
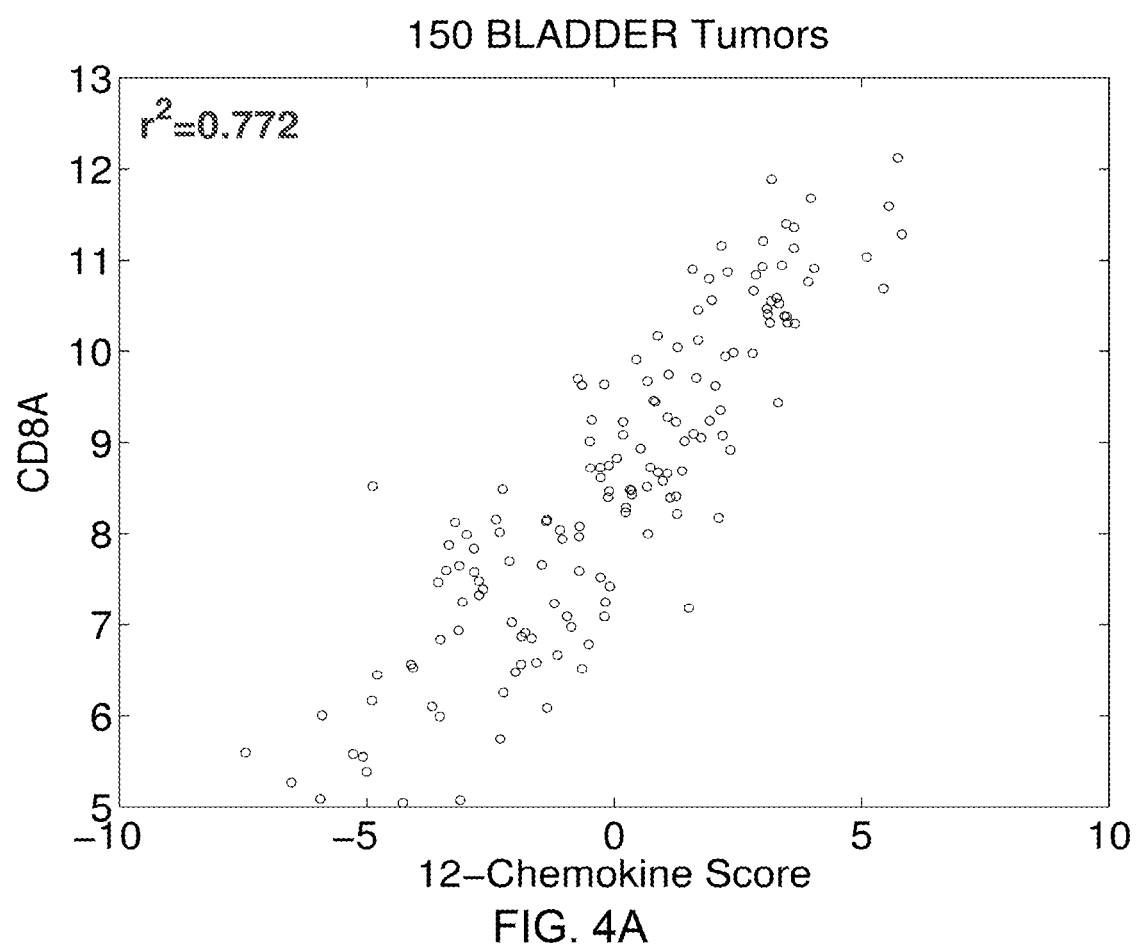
FIGS. 4A and 4B are plots showing that CD8A and Granzyme expression levels are correlated with the 12-Chemokine GES.
Figure 4B:
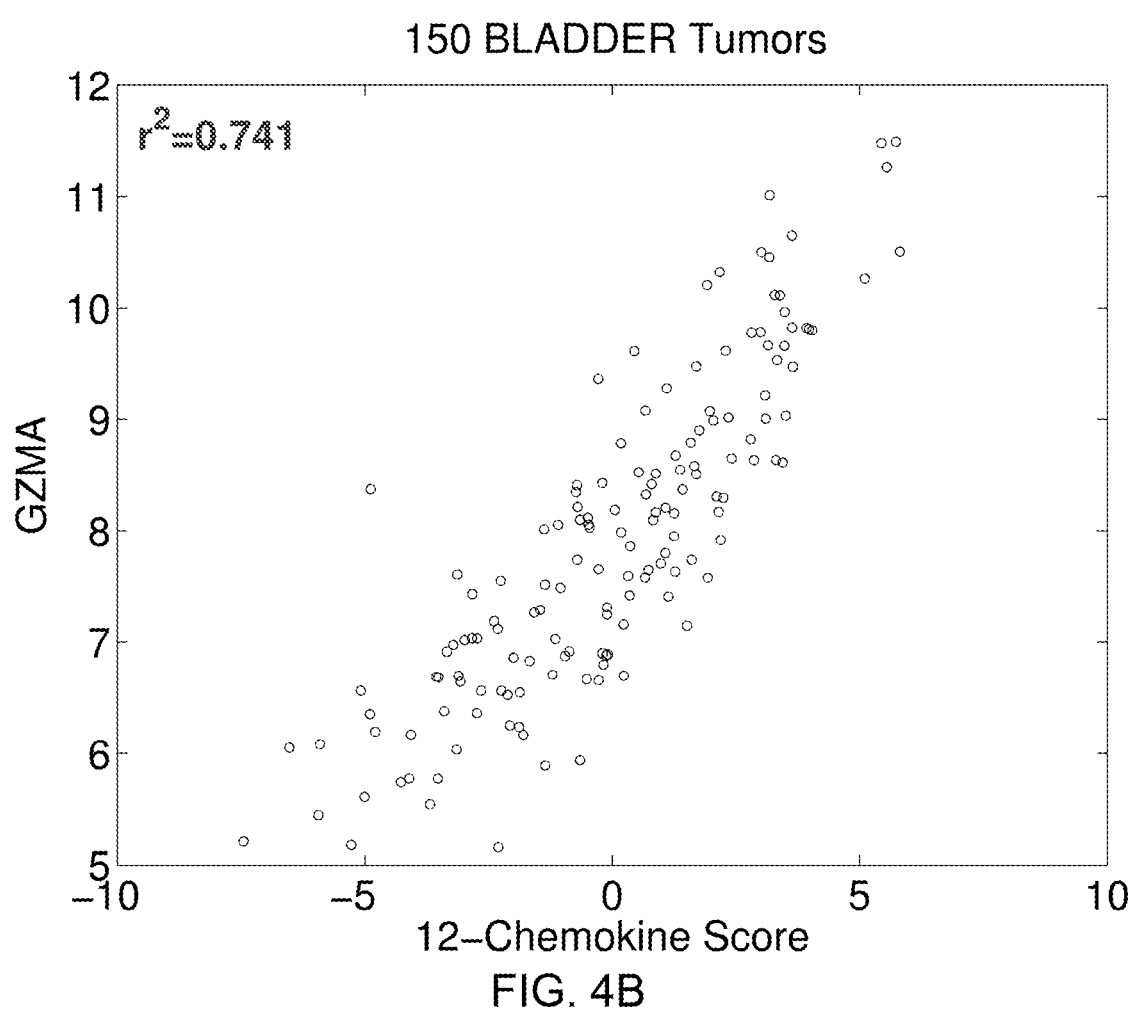

In addition, as shown in FIGS. 4A-B, CD8A and Granzyme expression was correlated with 12-Chemokine GES.

These results demonstrate a correlation between immune cell infiltration of tumors and clinical outcomes in bladder cancer. Characterization of these beneficial immune environments as well as deleterious ones is important for identification of prognostic and predictive markers. Chemokines and cytokines play an important role in shaping the immune environment, dictating the location, density and functional orientation of different immune cell populations.

In CRC high expression of genes encoding for chemokines CX3CL1, CXCL9 and CXCL10 was associated with the infiltration of memory T cells and effector T cells, particularly Th1 cells, and was associated with prolonged disease-free survival and overall survival. In UC CD8 tumor-infiltrating lymphocytes were show to be predictive of survival in muscle-invasive carcinoma. In the lung cancer local production of CCL19, CCL17, CCL22, CXCL13 and IL-16 is responsible for active recruitment of naive and memory T cells from the blood into TLS via high endothelial venules.

The 12-Chemokine GES identified a subset of patients with stage IV UC that generated an organized (tertiary lymphoid structures) immune response toward the invading tumor. The interaction of T cells with mature dendritic cells in tertiary lymphoid structures generated central memory and effector T cells in TLS. B cells interact with follicular dendritic cells to generate affinity maturation of immunoglobulins some of which may react with tumor-associated antigens. The CD4+ and CD8+ memory T cells that are generated migrate out through lymphatic vessels expressing CCL21 and migrate into the tumor or to the periphery where memory T cells may patrol for long periods of time to eventually target circulating malignant cells or nascent metastases.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a subject who has a urothelial carcinoma, the method comprising:
   obtaining cells from the carcinoma;
   determining mRNA expression levels of chemokine (C-C motif) ligand 2 (CCL2), CCL3, CCL4, CCL5, CCL8, CCL18, CCL19, CCL21, chemokine (C-X-C motif) ligand 9 (CXCL9), CXCL10, CXCL11, and CXCL13 in the tumor cells;
   comparing the expression levels to reference expression levels; and
   administering a treatment comprising an anti-cluster of differentiation 137 (CD137), anti-Programmed cell death protein 1 (PD1), anti-Programmed death-ligand 1 (PDL1), or anti-cytotoxic T-lymphocyte-associated protein 4 (CTLA-4) antibody to a subject who has expression levels above the reference expression levels.

2. The method of claim 1, wherein the subject is a human.

3. The method of claim 1, wherein comparing expression levels comprises calculating an expression score from the mRNA expression levels of CCL2, CCL3, CCL4, CCL5, CCL8, CCL18, CCL19, CCL21, CXCL9, CXCL10, CXCL11, and CXCL13 in the carcinoma, and comparing the expression score to a reference expression score.

4. The method of claim 1, wherein the treatment comprises an anti-PD1 antibody.

* * * * *